(12) United States Patent
Chang

(10) Patent No.: US 8,858,479 B2
(45) Date of Patent: Oct. 14, 2014

(54) ADJUSTABLE JOINT POSITIONING DEVICE

(75) Inventor: Ju-Sung C. Chang, Nantou County (TW)

(73) Assignee: Jone-Shou Industrial Co., Ltd., Nantou County (TW)

( * ) Notice: Subject to any disclaimer, the term of this patent is extended or adjusted under 35 U.S.C. 154(b) by 962 days.

(21) Appl. No.: 12/923,770

(22) Filed: Oct. 7, 2010

(65) Prior Publication Data

US 2012/0089064 A1    Apr. 12, 2012

(51) Int. Cl.
*A61F 5/00* (2006.01)
*A61F 5/01* (2006.01)

(52) U.S. Cl.
CPC .............. *A61F 5/0123* (2013.01); *A61F 5/01* (2013.01)
USPC .................... 602/16; 602/20; 602/23; 602/26

(58) Field of Classification Search
USPC ............... 602/5, 16, 20–29, 61–63; 128/882; 24/669, 702; D24/190–192
See application file for complete search history.

(56) References Cited

U.S. PATENT DOCUMENTS 6,557,177 B2 *   5/2003   Hochmuth ........................ 2/159
7,156,818 B2 *   1/2007   Salmon et al. .................... 602/5

FOREIGN PATENT DOCUMENTS

EP            297766  A1 *   1/1989

* cited by examiner

*Primary Examiner* — Kim M Lewis

(57) ABSTRACT

A joint positioning device includes a restriction frame having a first straight section, a second straight section and two transverse section connected between the first and second straight sections. Each of the two transverse sections includes multiple connection plates which are pivotably connected to each other so that the two transverse sections can be adjustable to meet the desired curvatures of the patients.

11 Claims, 6 Drawing Sheets

ADJUSTABLE JOINT POSITIONING DEVICE

BACKGROUND OF THE INVENTION (1) Field of the Invention

The present invention relates to a joint positioning device, and more particularly, to an adjustable joint positioning device.

(2) Description of the Prior Art

There are many joints in our body to connect bones and the joints allow the limbs to be bent to take different exercises. However, the joints are easily injured because they are used so frequently and the tendons are easily injured. Once the joints hurt, the operation of the bones are affected and the patients are restricted to move because the injured joints have to be well positioned.

A conventional joint positioning device is shown in FIG. 8 and generally includes a top support frame 70 and a bottom support frame 80. The top and bottom support frames 70, 80 are composed of two restriction frames 71, 81 and each restriction frame includes two straight sections 72/82 on two sides thereof and a transverse section 73/83 which is connected between the two straight sections 72/82 and are curved so as to match the curvature of the patient's thigh or calf. Soft pads 75, 85 and straps 76, 86 are connected to the inside of the top and bottom support frames 70, 80. The straps 76, 86 are tied to the thigh and calf to achieve the purpose of restriction of the joint.

The restriction frames 71, 81 each are an integral part so that the curvatures of the transverse sections 73, 83 have to match the size of the thigh and calf of the patients. Therefore, the manufacturers prepare the restriction frames 71, 81 with different curvatures of the transverse sections 73, 83. A high stocking cost is a pressure to the manufacturers so that only three or four sizes of the transverse sections 73, 83 are produced which obviously cannot meet the needs of patients. If the curvature of the transverse sections 73, 83 is not matched with the patients' thigh and/or calf, the patients feel uncomfortable and the result for wearing the joint positioning devices is not satisfied.

In addition, the restriction frames 71, 81 are integral parts and cannot be folded which occupy a large space and increase the cost of transportation.

The present invention intends to provide a joint positioning device wherein the curvature can be adjustable to match the patients of different sizes.

SUMMARY OF THE INVENTION

The present invention relates to a joint positioning device and includes a restriction frame having a first straight section, a second straight section and two transverse section connected between the first and second straight sections. Each of the two transverse sections includes multiple connection plates which are pivotably connected to each other so that the two transverse sections can be adjustable to meet the desired curvatures of the patients.

The primary object of the present invention is to provide a joint positioning device that is adjustable according to the curvatures of the legs of the patients who can comfortably wear the joint positioning devices.

Another object of the present invention is to provide a joint positioning device that can be disassembled for convenience of storage and transportation.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 1:
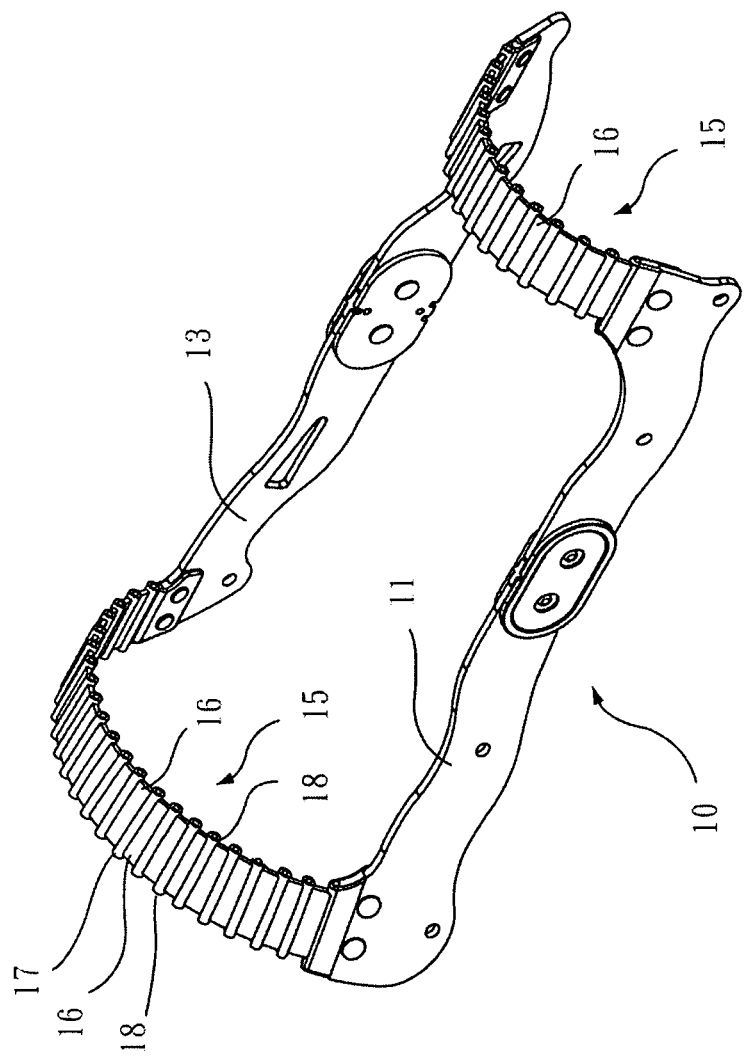
FIG. 1 is a perspective view to show the joint positioning device of the present invention.
Figure 2:
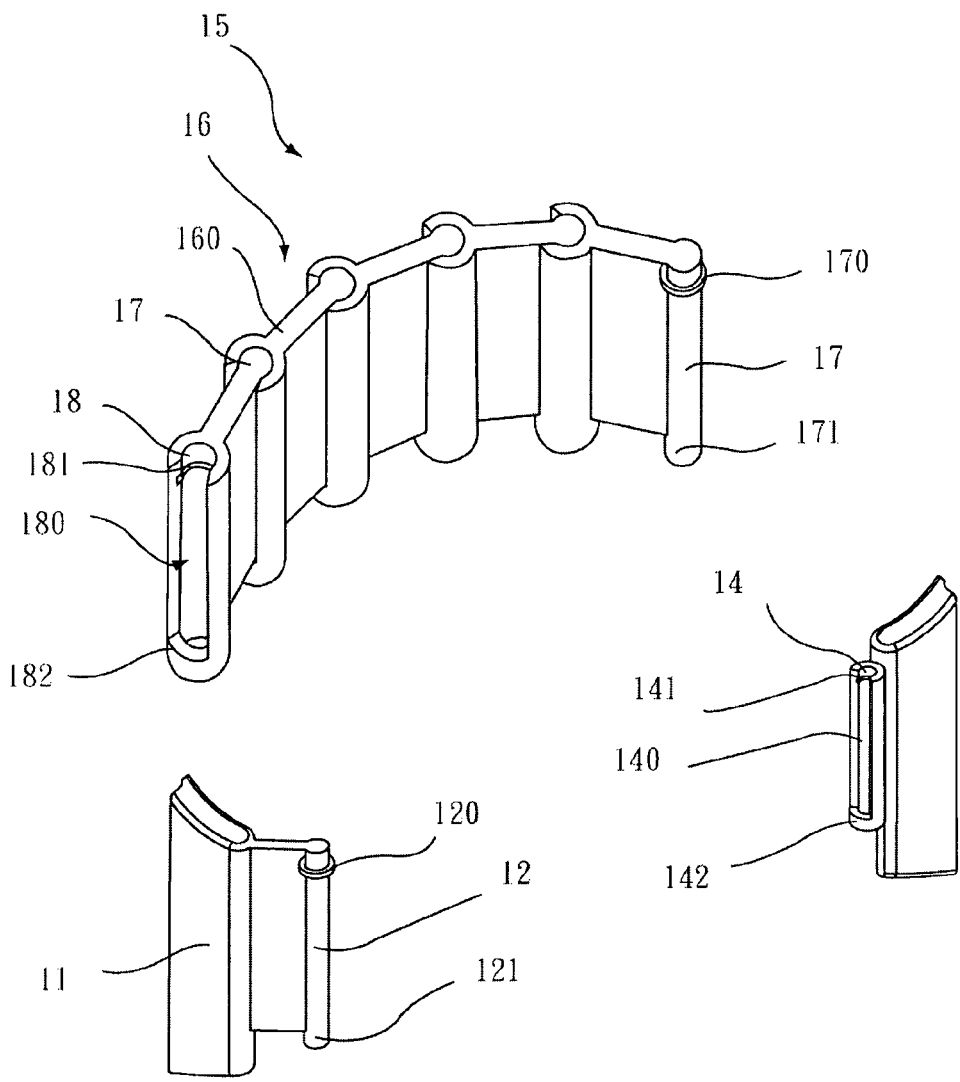
FIG. 2 is an exploded view to show the transverse section of the joint positioning device of the present invention.
Figure 3:
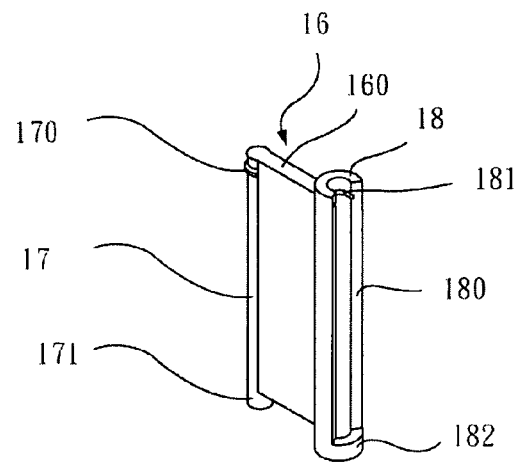
FIG. 3 is a perspective view to show the connection plate of the joint positioning device of the present invention.
Figure 4:
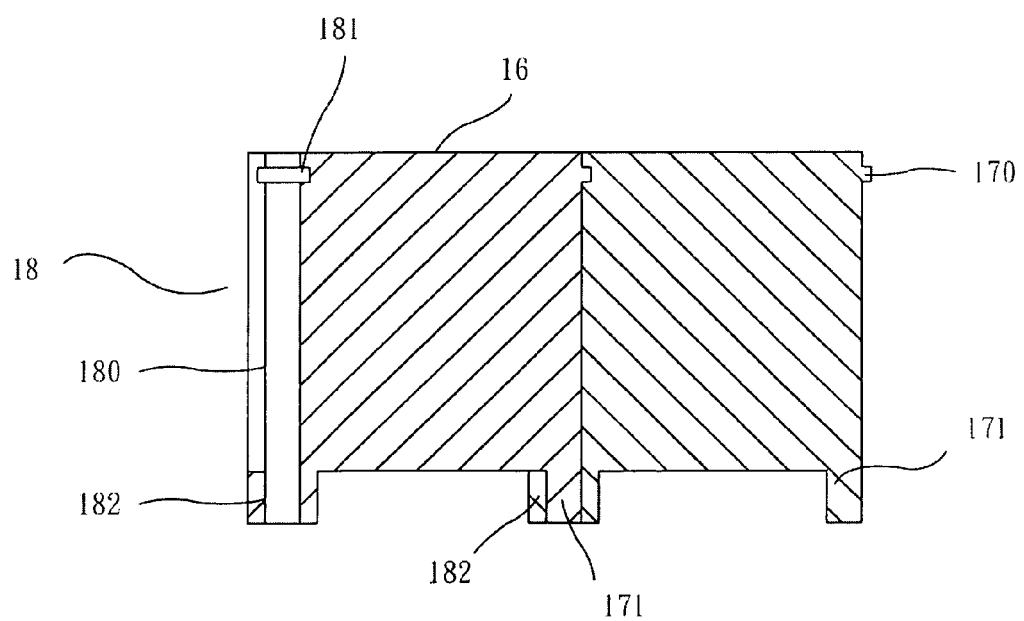
FIG. 4 is a cross sectional view of the connection of two connection plates of the joint positioning device of the present invention.

Referring to FIGS. 1 to 4, the joint positioning device of the present invention comprises a restriction frame 10 which includes multiple soft pads and straps to be positioned to the patient's thigh and calf to restrict the movement of the joint. The mediate portion of the restriction frame 10 can be pivoted and the curvature of the restriction frame 10 can be adjusted.

The joint positioning device of the present invention comprises a restriction frame 10 having a first straight section 11, a second straight section 13 and two transverse sections 15 which are connected between the first and second straight sections 11, 13. Each of the two transverse sections 15 includes multiple connection plates 16 which are pivotably connected to each other. Each of the connection plates 16 includes a pivot portion 17 and a reception portion 18 on two ends thereof. The pivot portion 17 has a flange 170 extending therefrom. The pivot portion 17 includes a protrusion 171 extending from a lower end thereof. The reception portion 18 has a slot 180 with which the pivot portion 17 is pivotably engaged. By this connection, the connected connection plates 16 are pivotally adjusted relative to each other. The reception portion 18 includes an engaging groove 181 defined in an inner periphery thereof so as to accommodate the flange 170 to position the two adjacent connection plates 16. The reception portion 18 includes a block part 182 which radially connected between two sides of the slot 180 and seals a lower end of the slot 180 so as to restrict the pivot portion 17 from disengaging from the slot 180.

The first straight section 11 has two pivot portions 12 on two ends thereof and the second straight section 13 has two reception portions 14 on two ends thereof. The pivot portions 12 and the reception portions 14 are located corresponding to the two transverse sections 15 respectively. The pivot portion 12 has a flange 120 extending therefrom and the pivot portion 12 has a protrusion 121 extending from a lower end thereof. The pivot portions 12 of the first straight section 11 each are connected with the reception portions 18 of the connection plates 16 on the transverse sections 15. The reception portion 14 has an engaging groove 141 with which the flange 170 is engaged to connect the two adjacent connection plates 16. The reception portions 14 of the second straight section 13 each have a slot 140 with which the pivot portion 17 of each of the transverse sections 15 is engaged. The pivot portion 14 has a restriction part 142 for enclosing the slot 140 to prevent the connection plate 16 from disengaging from the lower end thereof.

Figure 5:
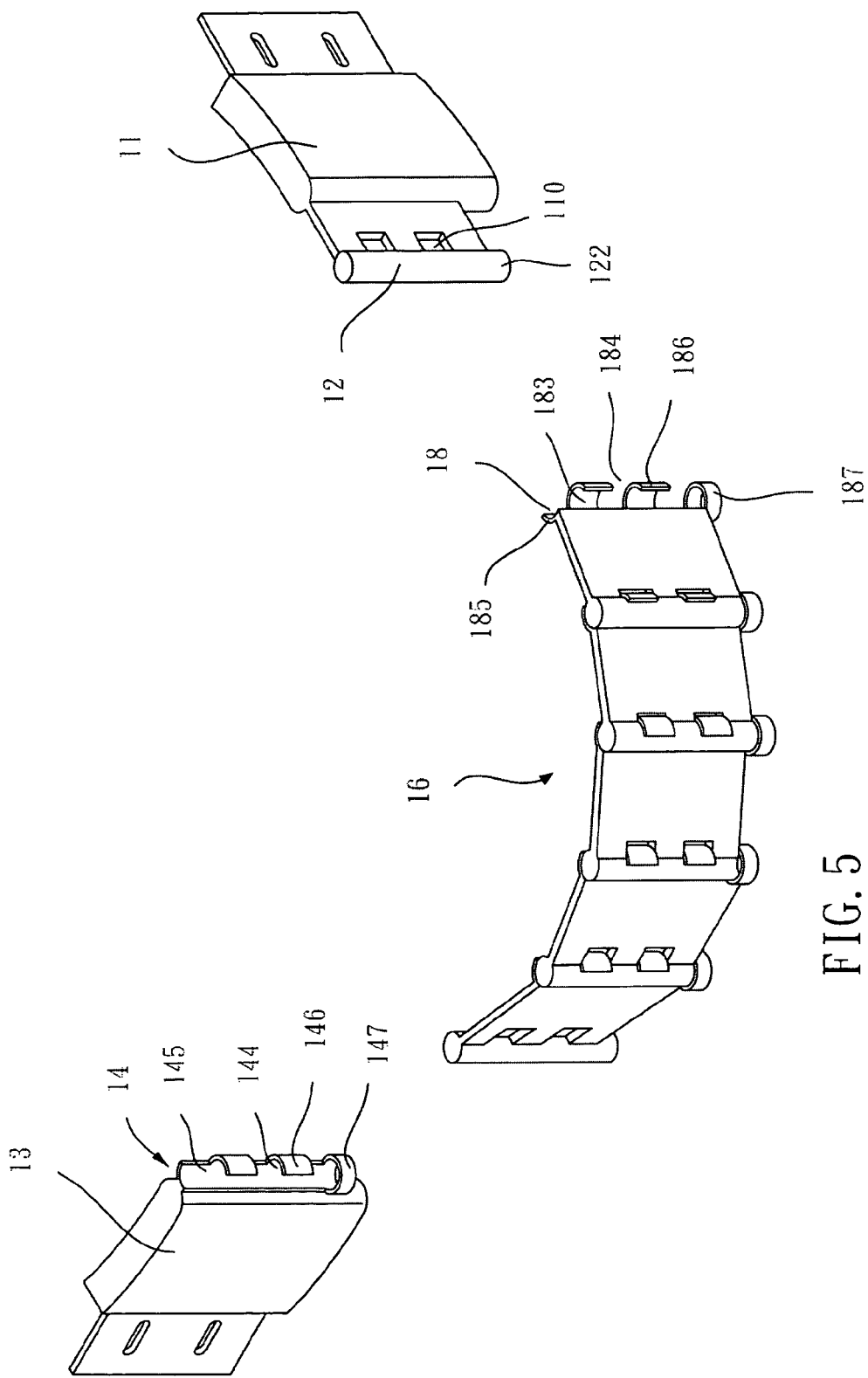
FIG. 5 is an exploded view to show the transverse section of the second embodiment of the joint positioning device of the present invention.
Figure 6:
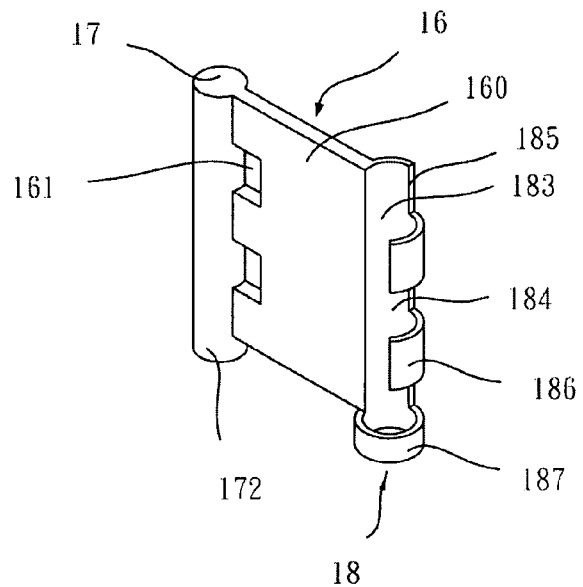
FIG. 6 is a perspective view to show the connection plate of the second embodiment of the joint positioning device of the present invention.
Figure 7:
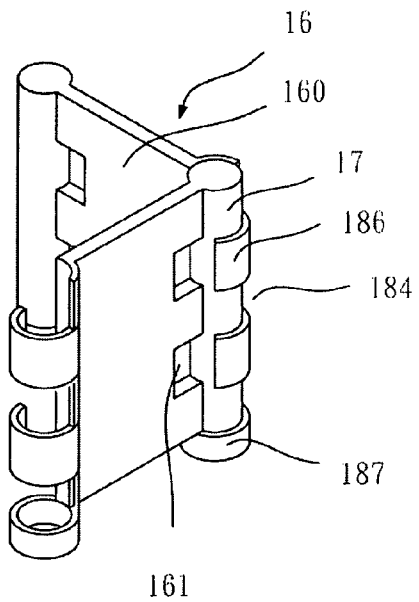
FIG. 7 is a perspective view of the connection of two connection plates of the second embodiment of the joint positioning device of the present invention.
Figure 8:
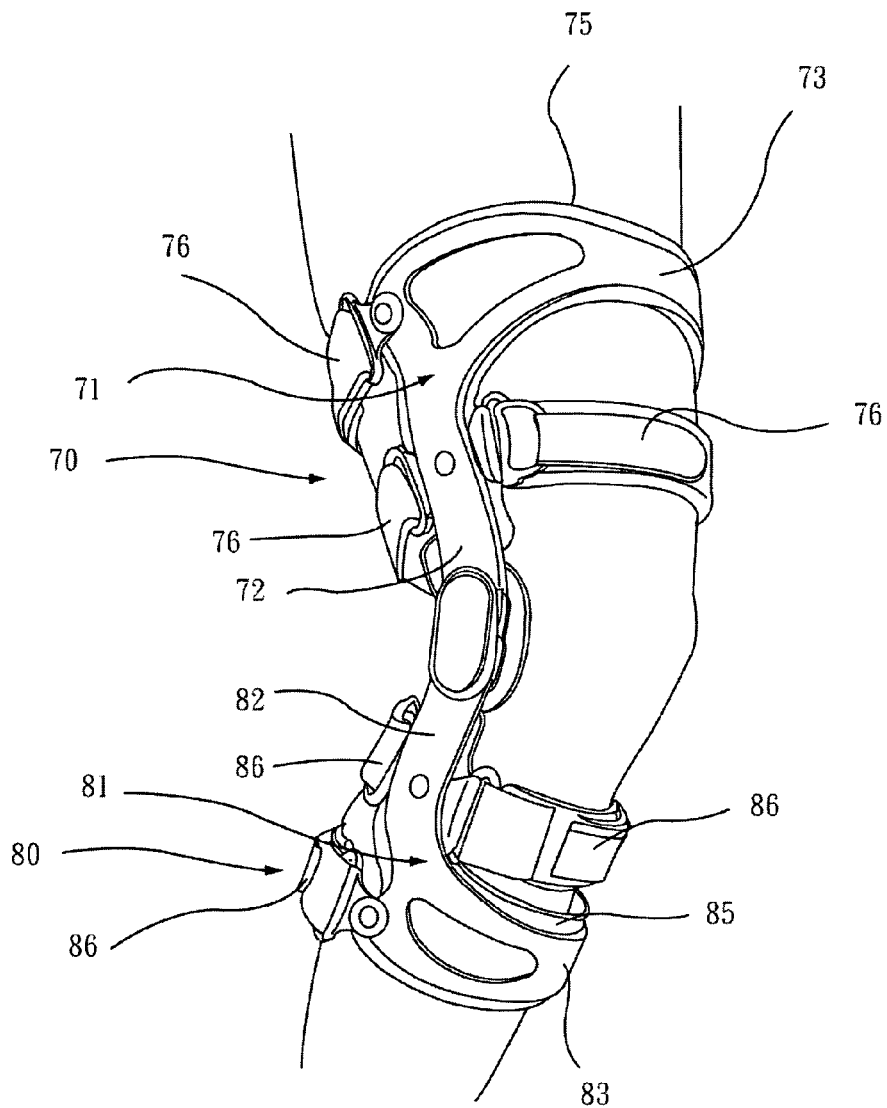
FIG. 8 is an exploded view to show the conventional joint positioning device.

FIGS. 5 to 7 show the second embodiment of the present invention, wherein the difference between the two embodiments is the connection between two connection plates 16. Multiple through holes 161 are defined through the body 160 of the connection plate 16 and the through holes 161 are located beside the pivot portion 17. The pivot portion 17 has a protrusion 172 extending from the lower end thereof. A slot 183 is defined in the reception portion 18 and located close to the body 160. At least one semi-closed slot 184 is defined in the reception portion 18 and located offset from the through holes 161. A block portion 185 is formed at the reception hole 18 and the at least one semi-closed slot 184. An angle between the block portion 185 on the reception portion 18 is over 180 degrees and less than 360 degrees measured from a conjunction of the slot 183 and the connection plate 16. The preferable angle is between 270-360 degrees. Multiple hooks 186 are formed at the reception portion 18 that has no semi-closed slot 184 and the hooks 146 are located corresponding to the through holes 161. When the pivot portion 17 of the connection plate 16 is engaged with the reception portion 18, the hooks 186 are engaged with the through holes 161. When the two adjacent connection plates 16 are pivoted to a desired angle, the block portion 185 stops the adjacent connection plate 16 to provide an angular positioning feature. In addition, the reception portion 18 has a restriction part 187 at a lower end thereof and which closes the slot 183 to prevent the adjacent connection plates 16 from disengaging from each other.

Multiple through holes 110 are defined through the first straight section 11 and located adjacent to the pivot portion 12 so that the reception portion 18 of the connection plate 16 on the transverse section 15 is engaged with the through holes 110 and the hooks 186 are engaged with the through holes 110. The pivot portion 12 has a protrusion 122 extending from a lower end thereof. A slot 143 is defined in the reception portion 14 of the second straight section 13 and multiple semi-closed slots 144 are defined in the reception portion 14 of the second straight section 13 and located offset from the through holes 161 of the connection plate 16. A block portion 145 is formed at the reception hole 14 and the at least one semi-closed slot 44. An angle between the block portion 145 on the reception portion 14 is over 180 degrees and less than 360 degrees measured from the conjunction of the slot 143 and the second straight section 13. The preferable angle is between 270-360 degrees. Multiple hooks 146 are formed at the reception portion 14 that has no semi-closed slot 144 and the hooks 146 are located corresponding to the through holes 161. When the pivot portion 17 of the connection plate 16 on the transverse section 15 is engaged with the reception portion 14 of the second straight section 13, the hooks 146 are engaged with the through holes 161. When the two adjacent connection plates 16 are pivoted to a desired angle, the block portion 145 stops the adjacent connection plate 16 to provide an angular positioning feature. In addition, the reception portion 14 has a restriction part 147 at a lower end thereof and which closes the slot 143 to prevent the adjacent connection plates 16 from disengaging from each other.

The slots 183, 143 are formed at the front side of the reception portions 18, 14. When the restriction frame 10 is assembled, the slots are located in opposite to the direction of rotation to prevent from separating the connection plates.

The connection plates 16 can be pivoted to match the curvature of the patient's thigh and calf. When adding the connection plates 16, simply inserting the pivot portion 17 into the reception portion 18 of the adjacent connection plate 16 so as to increase the length of the transverse section 15. The connection plates 16 can also be removed from the transverse section 15 by pivoting the pivot portion 17 in reverse direction to separate the two connection plates 16 so that the length of the transverse section 15 is reduced.

While we have shown and described the embodiment in accordance with the present invention, it should be clear to those skilled in the art that further embodiments may be made without departing from the scope of the present invention.

What is claimed is:

1. A joint Positioning device comprising:
a restriction frame having a first straight section, a second straight section and two transverse sections, the two transverse sections connected between the first and second straight sections and each of the two transverse sections including multiple connection plates which are pivotably connected to each other, each of the connection plates including a pivot portion and a reception portion on two ends thereof, the reception portion having a slot with which the pivot portion is pivotably engaged, the first straight section having two pivot portions on two ends thereof and the second straight section having two reception portions on two ends thereof, the pivot portions of the first straight section and the reception portions of the second straight portion located corresponding to the two transverse sections respectively, the pivot portions of the first straight section each being connected with the reception portions of the connection plates on the transverse sections, the reception portions of the second straight section each having a slot with which the pivot portion of each of the transverse sections is engaged, the pivot portion of each connection plate having a flange extending therefrom and the reception portion of each connection plate having an engaging groove with which the flange is engaged to connect the two adjacent connection plates, multiple through holes defined through a body of the connection plate and the through holes located beside the pivot portion corresponding thereto, at least one semi-closed slot defined in the reception portion, a block portion formed at the reception hole and the at least one semi-closed slot, multiple hooks formed at the reception portion that has no semi-closed slot and the hook being located corresponding to the at least one through hole.

2. The device as claimed in claim 1, wherein the pivot portion includes a protrusion extending from a lower end thereof and the reception portion includes a block part which radially connected between two sides of the slot and seals a lower end of the slot so as to restrict the pivot portion from disengaging from the slot.

3. The device as claimed in claim 1, wherein the slot is located in opposite to the pivot portion of the connection plate.

4. The device as claimed in claim 1, wherein the pivot portion has a flange extending therefrom and the reception portion has an engaging groove with which the flange is engaged to connect the two adjacent connection plates.

5. The device as claimed in claim 1, wherein the slot is located at a front end of the reception portion and beside a body of the connection plate.

6. The device as claimed in claim 1, wherein the first straight section has two pivot portions on two ends thereof and the second straight section has two reception portions on two ends thereof, the pivot portions and the reception portions are located corresponding to the two transverse sections respectively, the pivot portions of the first straight section each are connected with the reception portions of the connection plates on the transverse sections, the reception portions of the second straight section each have a slot with which the pivot portion of each of the transverse sections is engaged.

7. The device as claimed in claim 1, wherein an angle between the block portion on the reception portion is over 180 degrees and less than 360 degrees measured from a conjunction of the reception portion and the connection plate.

8. The device as claimed in claim 1, wherein the first straight section has two pivot portions on two ends thereof and the second straight section has two reception portions on two ends thereof, the pivot portions and the reception portions are located corresponding to the two transverse sections respectively, the pivot portions of the first straight section each are connected with the reception portions of the connection plates on the transverse sections, the reception portions of the second straight section each have a slot with which the pivot portion of each of the transverse sections is engaged.

9. The device as claimed in claim 6, wherein the first straight section has two pivot portions on two ends thereof and the second straight section has two reception portions on two ends thereof, the pivot portions and the reception portions are located corresponding to the two transverse sections respectively, the pivot portions of the first straight section each are connected with the reception portions of the connection plates on the transverse sections, the reception portions of the second straight section each have a slot with which the pivot portion of each of the transverse sections is engaged.

10. The device as claimed in claim 7, wherein multiple through holes are defined through the first straight section and located adjacent to the pivot portion, at least one semi-closed slot is defined in the reception portion of the second straight section, a block portion is formed at the reception hole and the at least one semi-closed slot, multiple hooks are formed at the reception portion that has no semi-closed slot and the hook is located corresponding to the at least one through hole.

11. The device as claimed in claim 10, wherein an angle between the block portion on the reception portion is over 180 degrees and less than 360 degrees measured from a conjunction of the reception portion and the second straight section.

* * * * *